US012808828B2

(12) United States Patent
Beck et al.

(10) Patent No.: US 12,808,828 B2
(45) Date of Patent: Nov. 24, 2026

(54) SOIL MOISTURE SENSOR WITH PARALLEL PLATE CAPACITANCE

(71) Applicant: Homedigy Inc., Los Altos, CA (US)

(72) Inventors: Jonathan Beck, Los Altos, CA (US); Kenneth Ng, Los Altos, CA (US); Lawrence Ying, Los Altos, CA (US)

(73) Assignee: HOMEDIGY, INC., Los Altos, CA (US)

( * ) Notice: Subject to any disclaimer, the term of this patent is extended or adjusted under 35 U.S.C. 154(b) by 217 days.

(21) Appl. No.: 18/734,983

(22) Filed: Jun. 5, 2024

(65) Prior Publication Data

US 2024/0402117 A1 Dec. 5, 2024

Related U.S. Application Data

(60) Provisional application No. 63/615,247, filed on Dec. 27, 2023, provisional application No. 63/471,001, filed on Jun. 5, 2023.

(51) Int. Cl.
*G01N 27/22* (2006.01)
*G01N 33/24* (2006.01)

(52) U.S. Cl.
CPC ......... *G01N 27/223* (2013.01); *G01N 27/226* (2013.01); *G01N 33/246* (2013.01)

(58) Field of Classification Search
CPC ... G01N 27/223; G01N 27/226; G01N 33/246
See application file for complete search history.

(56) References Cited

U.S. PATENT DOCUMENTS 5,479,104 A * 12/1995 Cambell .............. G01N 27/048 324/663
2009/0302870 A1* 12/2009 Paterson ................ G01N 33/24 324/670
2016/0183484 A1* 6/2016 Richings, Sr. ....... A01G 25/167 239/11
2019/0271656 A1* 9/2019 Pruessner ............ G01N 33/246
2022/0003744 A1* 1/2022 Kameoka ............. G01N 27/223

* cited by examiner

*Primary Examiner* — Akm Zakaria
(74) *Attorney, Agent, or Firm* — Nolte Lackenbach Siegel

(57) ABSTRACT

A soil moisture sensor includes a power source, a parallel plate capacitance sensing element, and an electronics unit. The parallel plate capacitance sensing element is powered by the power source and is adapted for ground insertion to generate and transmit capacitance data. The electronics unit is powered by the power source to: receive the capacitance data transmitted from the parallel plate capacitance sensing element; process the received capacitance data; and communicate the processed capacitance data off sensor.

22 Claims, 9 Drawing Sheets

SOIL MOISTURE SENSOR WITH PARALLEL PLATE CAPACITANCE

CROSS REFERENCE TO RELATED APPLICATION

The priority to and benefit of co-pending U.S. Patent Application Ser. No. 63/471,001, filed Jun. 5, 2023, the entire contents of which is hereby incorporated by reference as if fully set forth herein.

TECHNICAL FIELD

This disclosure relates generally to soil moisture sensors.

BACKGROUND

This section of this document introduces information about and/or from the art that may provide context for or be related to the subject matter described herein and/or claimed below. It provides background information to facilitate a better understanding of the various aspects of the present disclosure. This is a discussion of "related" art. That such art is related in no way implies that it is also "prior" art. The related art may or may not be prior art. The discussion in this section of this document is to be read in this light, and not as admissions of prior art.

Soil moisture is inextricably linked to the health of vegetation, particularly landscaped vegetation. It can also be important to the health of structures. For example, the soil moisture (or lack thereof) can cause certain types of soils to expand or contract. Structures constructed on such soils may experience displacement because of such expansion and compaction. Soil moisture may be of interest in still other contexts. For another example, storage of liquids such as refined hydrocarbons or wastewater are sometimes accompanied by concerns that the storage containers might leak. Soil moisture sensors might be used in some cases to monitor such storage for leaks.

Accordingly, soil moisture sensors may be used in many contexts. The landscaping uses may be most prominent, but there are other uses outside of landscaping and in industrial contexts in which they may be used. Soil moisture sensors are consequently known and well used. However, the art always welcomes improvements in the technology.

SUMMARY

The present disclosure includes apparatuses and methods associated with a soil moisture sensor using capacitive measurements. The soil moisture sensor accurately measures moisture data as a function of depth, permitting determination of both the surface moisture as well as the root level moisture and, in illustrated embodiments, a gradient therebetween. Such determinations permit identification of both watering and drying trends, thereby allowing a system to predict the need for watering and give more accurate watering suggestions. In addition, the surface area of the capacitance regions are surface area matched, for more system accuracy.

In a first aspect, a soil moisture sensor comprises a power source, a parallel plate capacitance sensing element, and an electronics unit. The parallel plate capacitance sensing element is powered by the power source and adapted for ground insertion to generate and transmit capacitance data. The electronics unit is also powered by the power source to receive the capacitance data transmitted from the parallel plate capacitance sensing element; process the received capacitance data; and communicate the processed capacitance data off sensor.

In a second aspect, a method for monitoring soil moisture comprises: disposing a soil moisture sensor in the ground, the soil moisture sensor comprising a parallel plate capacitance sensing element including a parallel plate capacitor; cyclically charging and discharging the parallel plate capacitor of the parallel plate capacitance sensing element; determining the soil moisture from the capacitance characteristics of the parallel plate capacitor as the parallel plate capacitor is cyclically charged and discharged; and transmitting the determined soil moisture off sensor.

In a third aspect, a system for monitoring soil moisture in a preselected area, the system comprises a plurality of soil moisture sensors, a communications system, and a remote computing system. The soil moisture sensors are disposed in the ground in the preselected area. Each of the soil moisture sensors further comprises a power source, a parallel plate capacitance sensing element, and an electronics unit. The parallel plate capacitance sensing element is powered by the power source and adapted for ground insertion to generate and transmit capacitance data from a plurality of depths at the respective location of the soil moisture sensor. The electronics unit is also powered by the power source to: receive the capacitance data transmitted from the parallel plate capacitance sensing element; process the received capacitance data; and communicate the processed capacitance data off sensor. Each soil moisture sensor transmits the respective soil moisture data over the communications system. The remote computing system receives the transmitted soil moisture data over the communications system and monitors the soil moisture condition of the preselected area.

In a fourth aspect, a method for monitoring soil moisture, comprising: disposing a plurality of soil moisture sensors in the ground in a preselected area, each of the soil moisture sensor comprising a parallel plate capacitance sensing element including a plurality of parallel plate capacitors disposed as different depths in the soil; cyclically charging and discharging the parallel plate capacitors of the parallel plate capacitance sensing elements; determining the soil moisture from the capacitance characteristics of the parallel plate capacitors as the parallel plate capacitors are cyclically charged and discharged; and transmitting the determined soil moisture off sensor over a communications system to a remote computing system for monitoring.

The above presents a simplified summary of the presently disclosed technique as claimed below in order to provide a basic understanding of some aspects of the presently disclosed technique. This summary is not an exhaustive overview of the presently disclosed technique. It is not intended to identify key or critical elements of the presently disclosed technique or to delineate the scope of the presently disclosed technique. Its sole purpose is to present some concepts in a simplified form as a prelude to the more detailed description that is discussed later.

BRIEF DESCRIPTION OF THE DRAWINGS

In the drawings, like reference numbers generally indicate identical, functionally similar, and/or structurally similar elements.

Figure 1A:
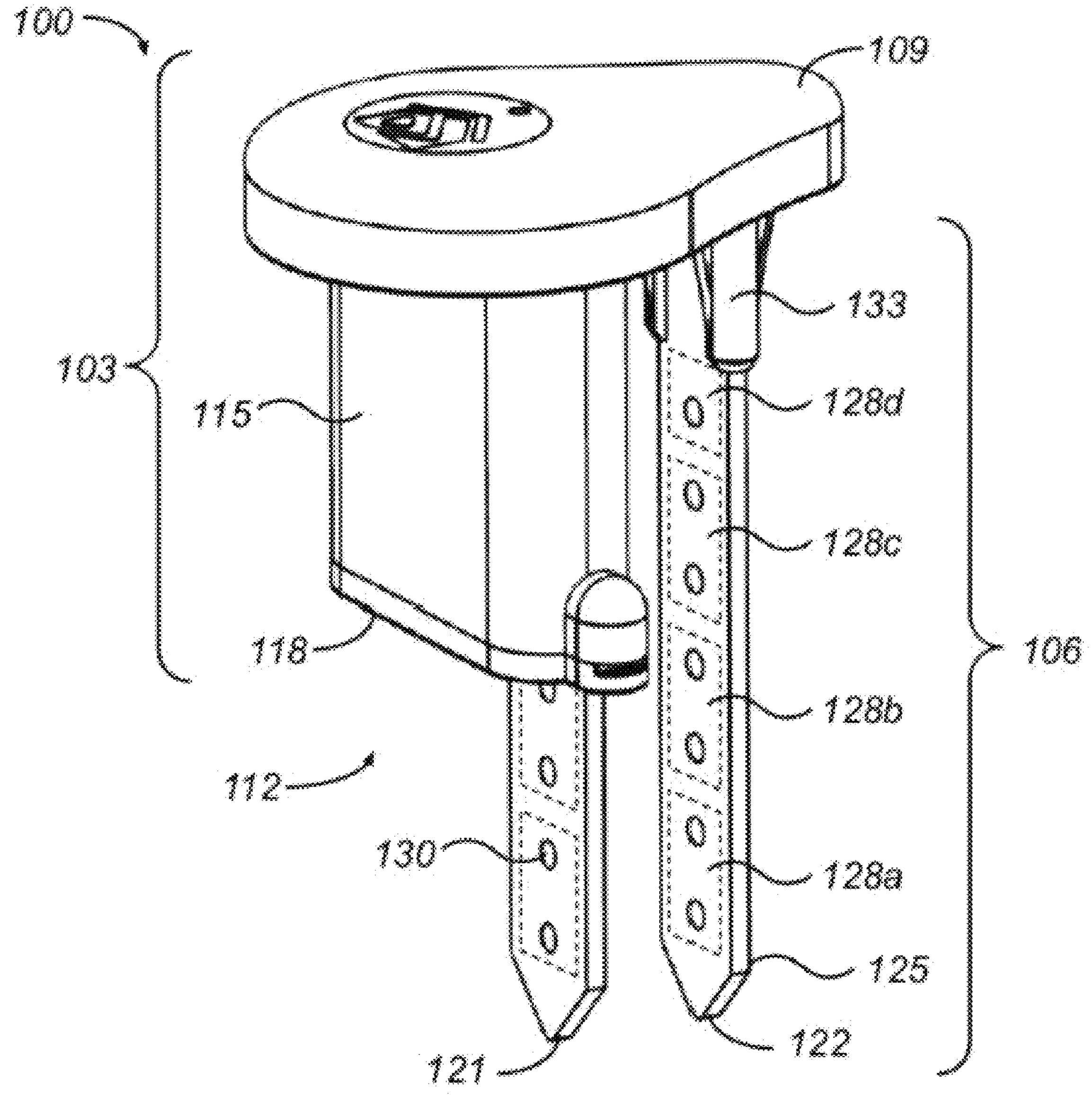
FIG. 1A and FIG. 1B depict one particular implementation of a soil moisture sensor in accordance with one or more embodiments in a perspective view showing the chassis and the parallel plate capacitance sensing element.

While the disclosed subject matter is susceptible to various modifications and alternative forms, the drawings illustrate specific implementations described in detail by way of example. It should be understood, however, that the description herein of specific examples is not intended to limit that which is claimed to the particular forms disclosed, but on the contrary, the intention is to cover all modifications, equivalents, and alternatives falling within the spirit and scope of the appended claims.

DETAILED DESCRIPTION

Illustrative examples of the subject matter claimed below are disclosed. In the interest of clarity, not all features of an actual implementation are described for every example in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Some conventional soil moisture sensors use resistive techniques for measuring soil moisture content. However, capacitive sensing tends to be more accurate and so most convention soil moisture sensors use capacitive sensing. Capacitive sensing techniques nevertheless experience very small capacitance deltas and are susceptible to noise.

Conventional soil moisture sensors therefore typically measure capacitance between two pieces of metal closely fixed to the same fixed, rigid structure in a way that creates an extremely small gap between the two pieces of metal. One piece of metal is charged and the other grounded to create a capacitance between the two through the soil. This capacitance is measured using side contact between the metal pieces and the soil. The small gap helps ensure a large capacitance value so that the capacitance value is easier to sense and the rigid structure helps ensure that the capacitance value stays relatively constant.

The presently disclosed and claimed soil moisture sensor employs capacitive sensing with a different approach. The conductive plates are much larger and spaced further apart (e.g., 2 cm-6 cm apart) than is found in conventional soil moisture sensors. The separation between conductive plates permits the sensor to sandwich the soil between the conductive plates so that, instead of measuring the capacitance of the soil moisture touching the sides of the conductive plates, the sensor is now measuring capacitance in the volume of the soil sandwiched between the two conductive plates. For present purposes, the type of capacitive sensing practiced in the present soil moisture sensor in which the soil moisture in a volume of soil sandwiched between two conductive plates shall be referred to as "capacitive displacement sensing over free space". Physically sandwiching soil in between the conductive plates allows measurement of a much large soil volume, which results in higher noise rejection, more stable readings, and much higher soil moisture detection capability across different soil types than is possible with the conventional design using the side-contact approach described above.

There are one or more parallel capacitor charging areas, or capacitors, as described more fully below, on each probe. These can also be referred to as "sensor area patches". One of the conductive plates on side of each sensor area patch is grounded to minimize electrical and parasitic noise. The other conductive plate on the other side of the sensor is then cyclically charged and allowed to discharge. The cyclical charging side can be either positive or negative voltage.

Thus, the physics works by quickly charging one side of the capacitor while keeping the other side grounded. The charged side is then allowed to discharge with a resistor that is connected in series to the physically large capacitor charging area. The RC decay rate is then measured, the capacitance and the soil dielectric constant determined therefrom, and the soil moisture content determined from the soil dielectric constant.

Figure 7A:
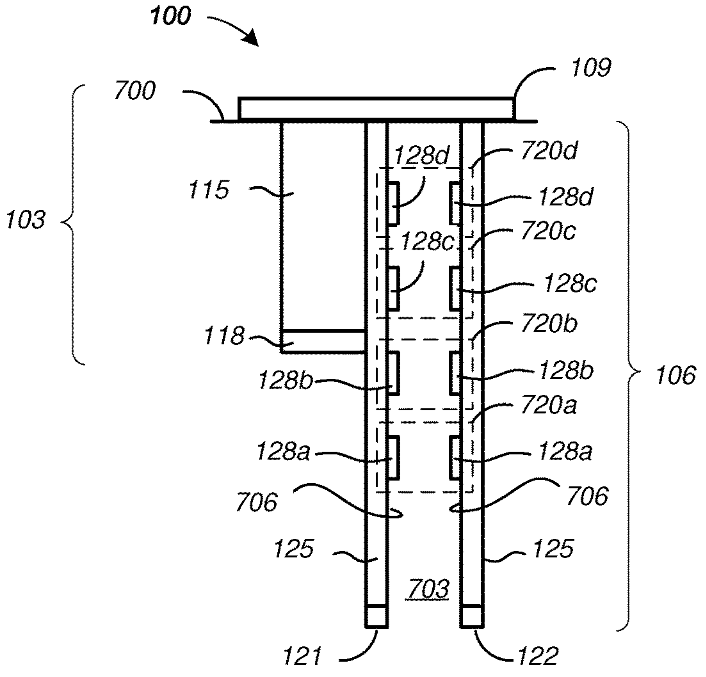
FIG. 7A, FIG. 7B, and FIG. 7C illustrate alternative placements for the electrically conductive plates of the capacitors in accordance with one or more embodiments in side, plan views.

Turning now to the drawings, FIG. 1A depicts one particular implementation of a soil moisture sensor 100 in accordance with one or more embodiments in a perspective view showing the chassis 103 and the parallel plate capacitance sensing element 106. FIG. 7A depicts the soil moisture sensor 100 in a side, plan view. Referring collectively to FIG. 1A and FIG. 7A, the chassis 103 includes a chassis cap 109 and a chassis body 112. The chassis body 112, in turn, comprises a compartment 115 for a power source and a cover plate 118 therefor.

Figure 1B:
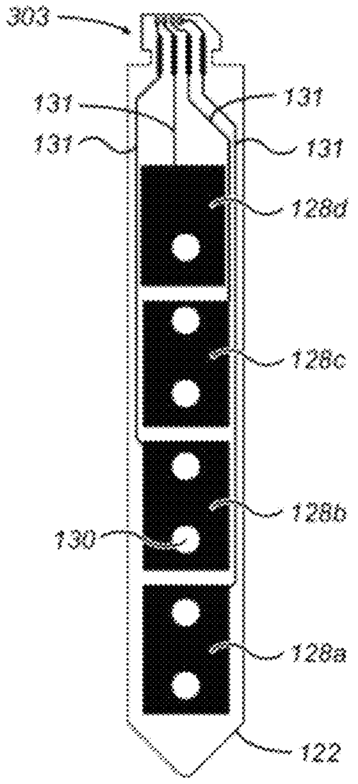
Figure 2:
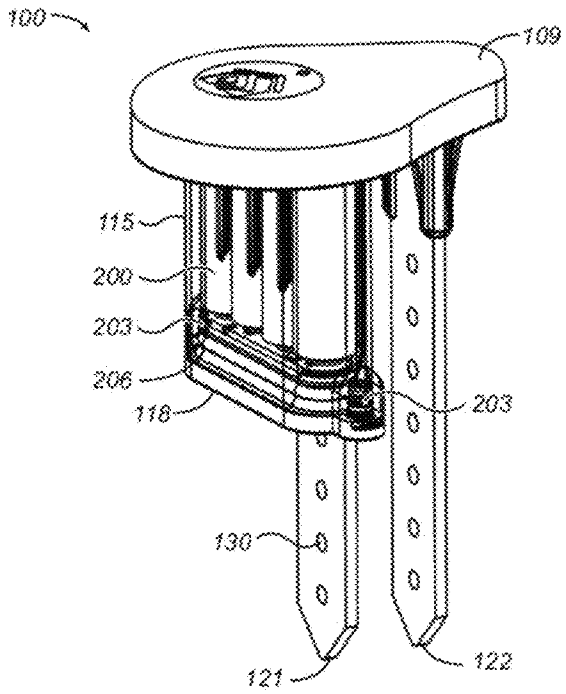
FIG. 2 is a partial cutaway of the soil moisture sensor of FIG. 1 in the same perspective view showing the power source, the sealed access to the power source, and the parallel plate capacitance sensing element.

FIG. 2 is a partial cutaway of the soil moisture sensor 100 of FIG. 1A in the same perspective view as FIG. 1A. Some aspects of the solid moisture sensor 100 shown in FIG. 1A-FIG. 1B are omitted from FIG. 2 for the sake of clarity. For example, the electrically conductive plates 128*a*-128*d* are omitted.

The compartment 115 is cut away to show the power source 200. In the illustrated embodiment, the power source 200 includes four batteries. The batteries may be, for example, rechargeable Lithium ("Li") ion, Nickel-Cadmium ("NiCd"), or Nickel-metal hydride ("NiMH") batteries, Alkaline batteries, or some other battery technology. The power source 200 may be rechargeable, replaceable, or both rechargeable and replaceable. Some embodiments in which the power source 200 is rechargeable may include solar power charging elements (not shown) or an electrical port (not shown) for recharging. Alternatively, the batteries may be removed from the compartment 115 and charged using an electrical outlet (not shown) delivering line power from the electrical grid.

In the illustrated embodiment, the power source 200 is removable for recharging and/or replacement. To remove the power source 200 from the compartment 115, a pair of fasteners 203 are removed so that the cover plate 118 may be disassembled from the compartment 115 and the power source 200 removed. The power source 200 may then be recharged or replaced. The power source 200 may then be returned to the compartment 115 and the cover plate 118 reassembled to the compartment 115.

As the fasteners 203 are refastened, the cover plate 118 compresses an elastomeric sealing element 206. The elastomeric sealing element 206 may be, for example, an O-ring or a gasket in some embodiments. The compressed elastomeric sealing element 206 provides a fluid tight seal between the cover plate 118 and the compartment 200. The cover plate 118, fasteners 203, and elastomeric sealing element 206 thereby provide sealed access to the power source 200. More particularly, this access is sealed against fluid, moisture, and plant root penetration. Additionally, the cover plate 118 is designed to ensure moisture or water condensation would flow outward to prevent mold buildup and root intrusion.

Referring now collectively to FIG. 1A, FIG. 2, and FIG. 7A, the parallel plate capacitance sensing element 116 includes a pair of sensor probes 121, 122. The sensor probes 121, 122 may have either a mirrored or non-mirrored construction. In this embodiment, the sensor probe 121 closest to the power source 200 is grounded while the sensor probe 122 furthest from the power source 200 is the charging element. Thus, the one side may be referred to as the "ground side" or "grounded side" and the other side may be referred to as the "charged side". The charging element (i.e., the sensor probe 122, in this embodiment) may be either positively charged or negatively charged. In this embodiment, the sensor probe 121 may also be referred to as the "ground element".

The conductive plates 128*a*-128*d* of the sensor probe closer to the power source 200, sensor probe 121 in this embodiment, have a larger overall conductive area than those on the other sensor probe 122 furthest away from the power source 200. This maximizes noise reduction. The "larger overall area" includes the conductive area to which it is connected on the main printed circuit board 312 containing the electronics unit 300, shown in FIG. 3. The overall conductive area of the charging element—i.e., the sensor probe 122—is smaller than that of the grounded element—i.e., the sensor probe 121, again to minimize noise. In this context, the terms "larger" and "smaller" are relative to the overall areas of the conductive materials for the respective sensor probes 121, 122 as described above.

The sensor probe 122 comprises a printed circuit board 125 having at least one electrically conductive plate 128*a* mounted thereon. The illustrated embodiment employs four electrically conductive plates 128*a*-128*d*, but other embodiments may use other numbers. The number of electrically conductive plates in any given embodiment is theoretically unlimited although practical considerations arising from the intended use will limit the length of the printed circuit board 125 and, thus, the number of electrically conductive plates. The electrically conductive plates 128*a*-128*b* in the illustrated example are fabricated from Copper, although other electrically conductive materials may be used.

The electrically conductive plates 128*a*-128*d* may be mounted by etching the Copper onto the printed circuit board that comprises the respective sensor probe 121, 122. The etching may use etching techniques standard in the fabrication of printed circuit boards for, for instance, traces, but other techniques may be used in other embodiments. Note that the standard etching techniques permit the entire sensor probes 121, 122 to be printed using conventional techniques. The "ground side" probe can also be manufactured using a single piece of insulated or coated piece of metal, since it is a single conductor without the need for multiple sensing areas.

Figure 9:
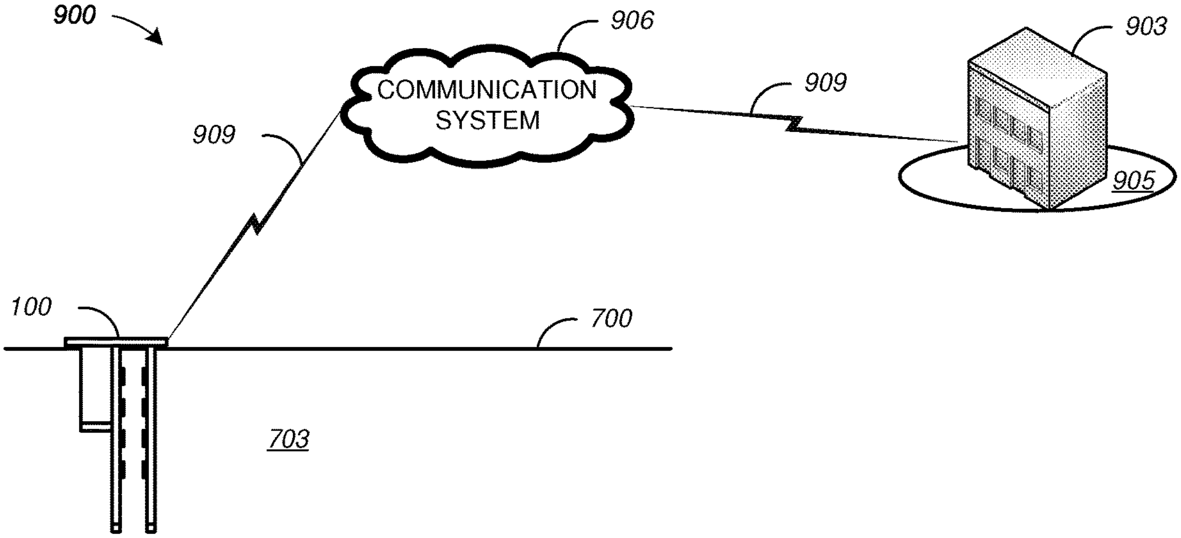
FIG. 9 depicts a soil moisture sensor inserted into the ground and communicating soil moisture data off sensor to a remote computing system through a communications system in accordance with one or more embodiments.

As best shown in FIG. 7A, each electrically conductive plate 128*a*-128*d* of the sensor probe 122 is paired with another electrically conductive plate 128*a*-128*d*, respectively, mounted to the other sensor probe 121. When the soil moisture sensor 100 is inserted into the ground 700, as shown in FIG. 9, the soil 703 acts as a dielectric. The paired electrically conductive plates 128*a*-128*a*, 128*b*-128*b*, 128*c*-128*c*, 128*d*-128*d* then each define a respective parallel plate capacitor 720*a*-720*d*.

The sensor probe 122 also includes an electrical trace 131 for each of the electrically conductive plates 128*a*-128*d*. In this embodiment, the electrical traces 131 are formed on the printed circuit board 125 as best shown in FIG. 1B. The back of the printed circuit board 125 for the sensor probe 122 is not visible in the drawings, but the electrical traces 131 on the back of the printed circuit board 125 for the sensor probe 121 are visible. The electrical traces 131 are in or on the printed circuit board 125 and extending from the respective electrically conductive plates 128*a*-128*d* to the electronics unit to be discussed below.

The illustrated embodiments include a plurality of holes 130, or through-bores, formed in sensor probes 121-122, only one of which is indicated. The holes 130 improve the "grip", or the strength of the contact, between the sensor probes 121-122 and the soil in which the soil moisture sensor 100 is inserted as shown in FIG. 7A. The illustrated soil moisture sensor 100 also includes at least one spike 133 that helps stabilize the position of the soil moisture sensor 100 relative to the ground into which it is inserted. Note that the holes 130 and the spike(s) 133 are optional and may be omitted in some embodiments. Furthermore, where the holes 130 and/or spikes 133 are used, different embodiments may use different numbers of each.

Figure 3:
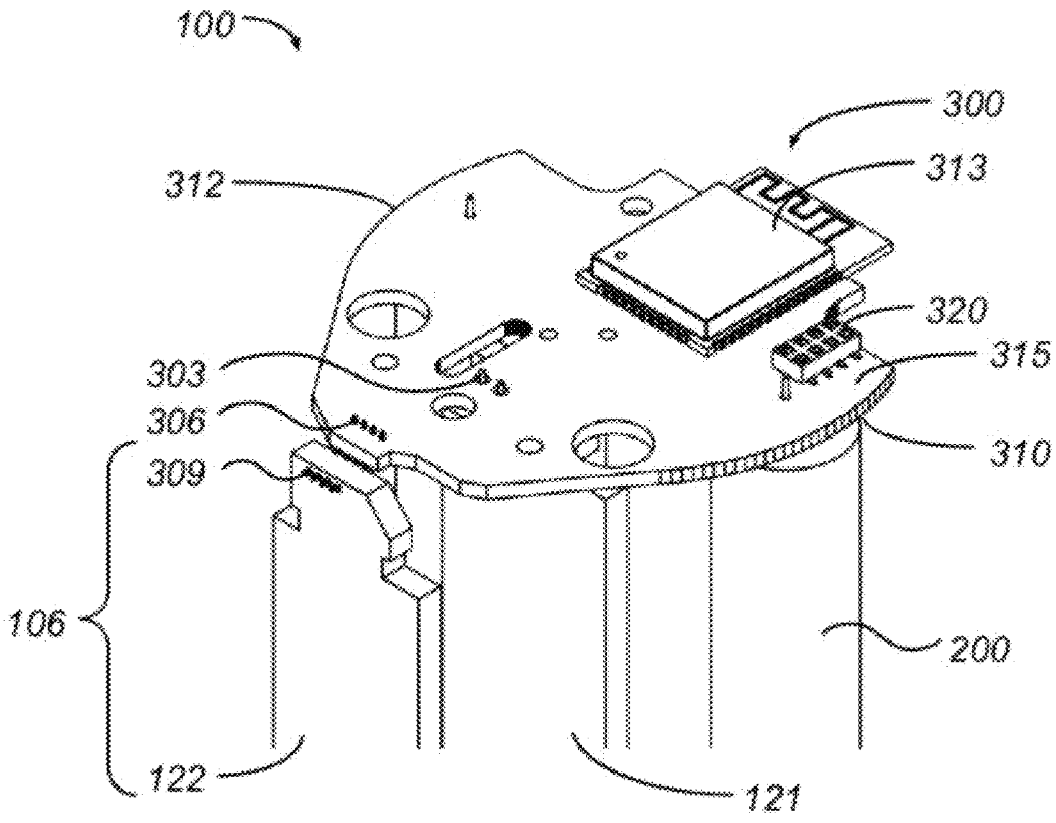
FIG. 3 is a cutaway of the view of the soil moisture sensor of FIG. 1 and FIG. 2 from a second perspective to illustrate selected features of the electrical aspects of the sensor, including portions of the electronics unit and the interconnects between the electronics unit and the parallel plate capacitance sensing element.

FIG. 3 is a cutaway of the view of the soil moisture sensor of FIG. 1A, FIG. 2, and FIG. 7A from a second perspective to illustrate selected aspects of the electrical aspects of the soil moisture sensor 100. The selected aspects include portions of the electronics unit 300 and the interconnects 303, 306, 309 between the electronics unit 300 and the parallel plate capacitance sensing element 106. A comparison with FIG. 1A reveals that the compartment 115 and chassis cap 109 have been cut away in FIG. 3.

Figure 4:
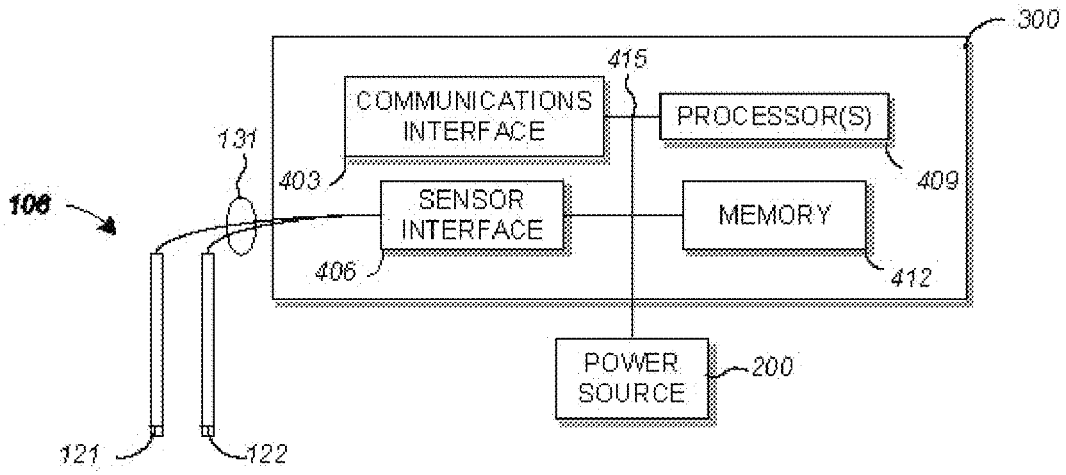
FIG. 4 is a schematic diagram of one particular implementation of the electronics unit in accordance with one or more embodiments.

FIG. 4 is a schematic diagram of one particular implementation of the electronics unit 300 in accordance with one or more embodiments. The electronics unit 300 includes at least a communications interface 403, a sensor interface 406, one or more processors 409, and a memory 412. These components all communicate over a bus system 415.

In general, it is contemplated by the present disclosure that soil moisture sensor 100 includes electronic components and/or electronic computing devices operable to receive, transmit, process, store, and/or manage data and information associated performing the functions thereof as described herein. This contemplation encompasses any suitable processing device adapted to perform computing tasks consistent with the execution of computer-readable instructions stored in a memory or a computer-readable recording medium. Also encompassed are any suitable sensor and/or communications interface for performing the ascribed functions for the soil moisture sensor 100 described herein.

The one or more processors 409 may be used for controlling the general operations of the soil moisture sensor 100, as well as processing data and information received through the sensor interface 406 and communicating that data and information off sensor through the communications interface 403. The one or more processors 409 may be any suitable processor-based resource. They may be, but are not limited to, a central processing unit ("CPU"), a hardware microprocessor, a multi-core processor, a single core processor, a field programmable gate array ("FPGA"), a controller, a microcontroller, an application specific integrated circuit ("ASIC"), a digital signal processor ("DSP"), or other similar processing device capable of executing any type of instructions, algorithms, or software for controlling the operation and performing the functions of patient monitor 102. In some embodiments, the one or more processors 110 may comprise a processor chipset including, for example and without limitation, one or more co-processors.

The memory 412 may be a single memory device or one or more memory devices at one or more memory locations that may include, without limitation, one or more of a random-access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk, various layers of memory hierarchy, or any other non-transitory computer readable medium. The memory 412 may be on-chip, off-chip, or some combination thereof depending on the implementation of the one or more processors 409. The memory 412 may be used to store any type of instructions and patient data associated with algorithms, processes, or operations for controlling the general functions and operations of the patient monitor 409.

The communications interface 403 may permit the soil moisture sensor 100 to directly or indirectly (via, for example, a monitor mount) communicate with one or more computing networks and devices, workstations, consoles, computers, monitoring equipment, alert systems, and/or mobile devices (e.g., a mobile phone, tablet, or other handheld display device). The communications interface 403 may include various interfaces, communication channels, cloud, antennas, and/or circuitry to permit wireless communications with such computing networks and devices. The communications interface 403 may be used to implement, for example, a BLUETOOTH® connection, an Infrared connection, a ZIGBEE® connection, a cellular network connection, a LoRa WAN connection, and/or a WIFI® connection with such computing networks and devices. Other example wireless communication connections implemented using the communication interface 403 include wireless connections that operate in accordance with, but are not limited to, IEEE802.11 protocol, a Radio Frequency For Consumer Electronics ("RF4CE") protocol, and/or IEEE802.15.4 protocol (e.g., ZigBee® protocol). In essence, any wireless communication protocol may be used without any requirement on minimum communication bandwidth or distance.

The sensor interface 406 may be implemented in hardware or combination of hardware and software and is used to connect via wired and/or wireless connections to the parallel plate capacitance sensing element 106 for gathering capacitance data. The data signals received from the parallel plate capacitance sensing element 106 may be analog signals. The sensor interface 406 may include amplifying and filtering circuitry as well as analog-to-digital ("A/D") circuitry that converts the analog signal to a digital signal using amplification, filtering, and A/D conversion methods. Thus, the sensor interface 108 is a component which may be configured to interface with the parallel plate capacitance sensing element 106 and receive sensor data therefrom.

Returning now to FIG. 3, some aspects of the electronics unit 300 are not immediately visible in that view because they are mounted to the underside 310 of the printed circuit board 312. For example, the communications interface 403 and the sensor interface 406, shown in FIG. 4, may be mounted to the printed circuit board 312. The electronics unit 300 includes a controller 313 mounted on the upper surface 315 of the printed circuit board 312. The controller 313 may comprise, in this example, the one or more processors 412 and memory 415, both shown in FIG. 4, the memory 415 being on chip with the one or more processors 412.

Note that in some embodiments all elements of the electronics unit 300 may be located on the same side 310, 315, whether the underside 310 or the top surface 315. In some embodiments, the entire electronics unit 300 may be implemented in a "system on a chip" so that there is only a single component to be mounted to the printed circuit board 312. However, the electronics unit 300 is implemented, the bus system 415 of FIG. 4 may be implemented accordingly and the interconnects 303, 306 are electrically connected to at least the sensor interface 406.

In the embodiment of FIG. 3, an electrical port 320 is shown mounted to the printed circuit board 315. The electrical port 320 mates with an external connector (not shown) so that through which the controller 313 may be programmed, or configured, during manufacture. The electrical port 313 may also be used to program/configure other active components of the electronics unit 300 in some embodiments. The present embodiment contemplates that the electrical port 320 will only be utilized during manufacture. However, in alternative embodiments, the electrical port 320 may be used to reprogram the controller 313 upon refurbishment or update once the chassis cap 109 is opened.

The illustrated embodiments of the soil moisture sensor 100 use multiple sealing strategies for both battery compartment and the chassis to protect against fluid intrusion from the surrounding environment during use. The chassis body 112, for example, uses the elastomeric seal 206 discussed above. In this case, the cover plate 118 is screwed into the compartment 115, which puts the elastomeric seal 206 into compression. The elastomeric seal 206 is fabricated from a commercial-grade silicone to create a watertight seal. They are designed against industrial-grade outgassing standards, which are much stricter than the IP67 rating for modern "waterproof" smartphones.

Figure 5:
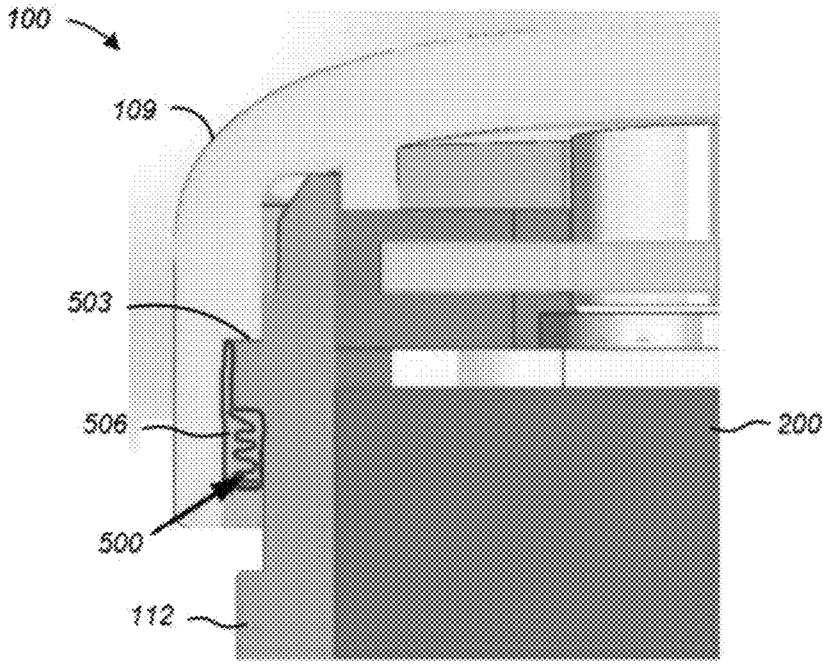
FIG. 5 is a cross-sectioned fragment of the soil moisture sensor of FIG. 1-FIG. 3 illustrating the seal between the chassis cap and the chassis body.

However, to seal the chassis cap 109 to the chassis body 112, a different strategy illustrated in FIG. 5 is used. FIG. 5 is a cross-sectioned fragment of the soil moisture sensor 100 of FIG. 1A-FIG. 3 illustrating the seal between the chassis cap 109 and the chassis body 112. Here, an industrial strength adhesive 500, for example, an epoxy or a polyurethane, is applied along the perimeter 503 between the chassis cap 109 and the chassis body 112. In order to aid the application of the adhesive a space or "well" 506 for the adhesive to set in is provided. This allows the 600 to be applied in a 360° around the perimeter 503 of the chassis body 112. This seal helps ensure that the soil moisture sensor 100 will function in the outside environment and will be protected from environmental moisture intrusion. The seal 500 is also flexible enough that impacts to the chassis cap 109 will not rupture the seal.

Figure 6:
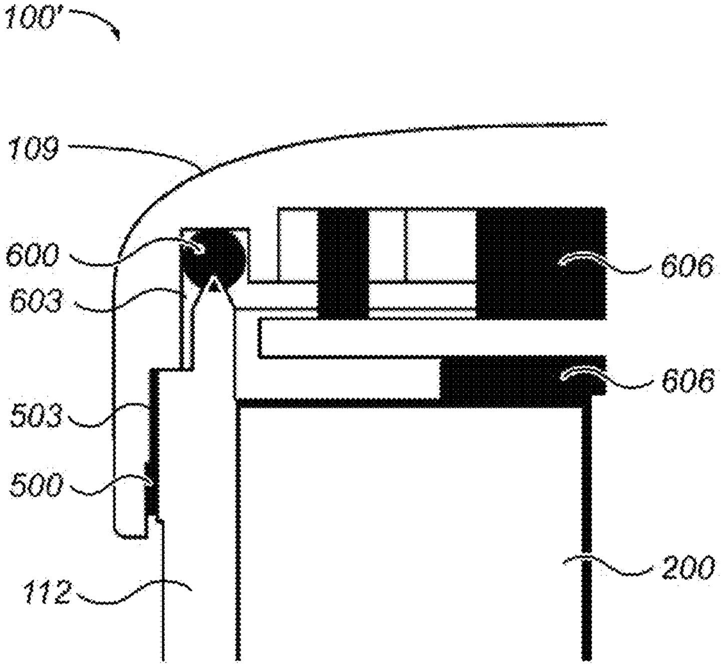
FIG. 6 is a cross-sectioned fragment of an alternative embodiment of the soil moisture sensor of FIG. 1-FIG. 3 illustrating the seal between the chassis cap and the chassis body.

Some embodiments nevertheless may use only elastomeric sealing elements instead to seal the chassis cap 109 to the chassis body 112 as shown in FIG. 6. FIG. 6 is a cross-sectioned fragment of the soil moisture sensor 100' of FIG. 1A-FIG. 3 in which an elastomeric sealing element 600 (e.g., an O-ring) is disposed in a well 603 between the chassis cap 109 and the chassis body 112. Some embodiments may use both the adhesive 500 and the elastomeric sealing element 600 to seal between the chassis cap 109 to the chassis body 112 as shown in FIG. 6.

Figure 7B:
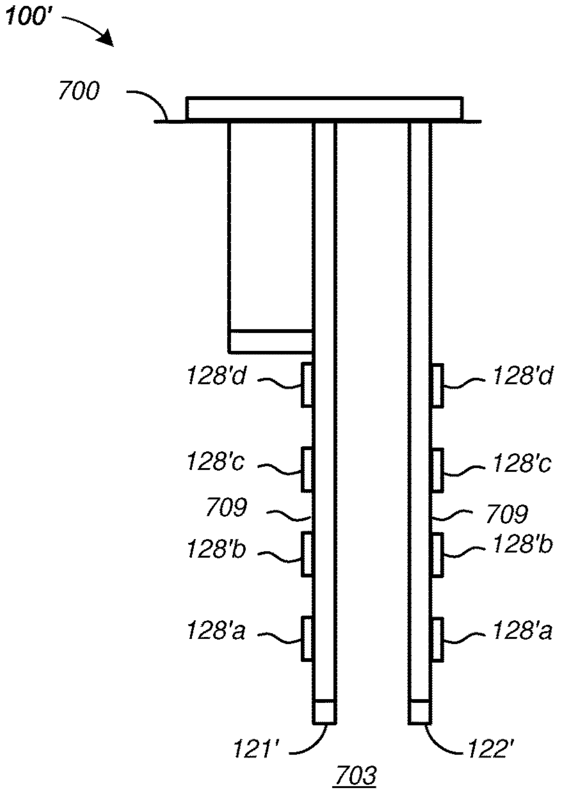
Figure 7C:
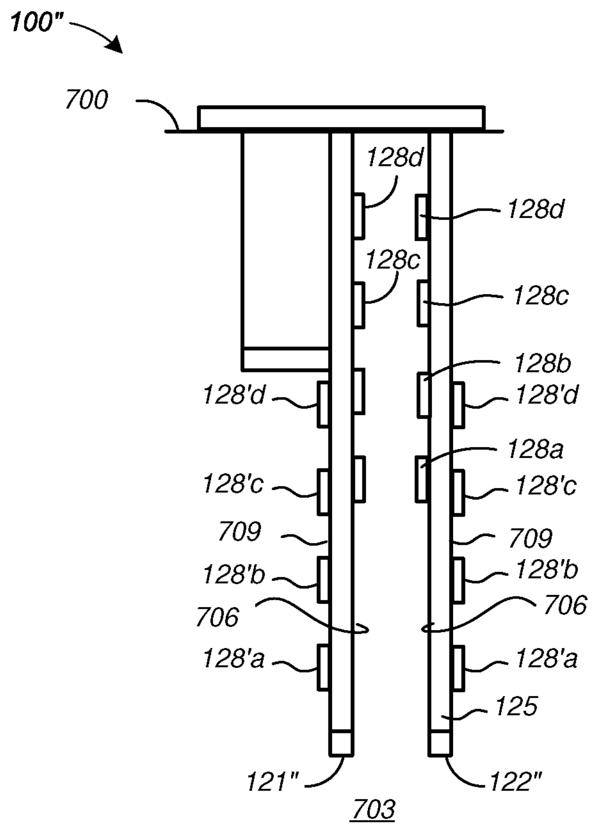

FIG. 7A, FIG. 7B, and FIG. 7C illustrate alternative placements for the electrically conductive plates of the capacitors in accordance with one or more embodiments in side, plan views. FIG. 7A was discussed briefly above with respect to the structure of the soil moisture sensor 100 as to the sensor probes 121, 122. As noted in that discussion, each set of paired plates 128*a*-128*a*, 128*b*-128*b*, 128*c*-128*c*, 128*d*-128*d* define a respective parallel plate capacitor 720*a*-720*d* when the soil moisture sensor 100 is inserted into the ground 700 such that the soil 703 performs as a dielectric. Note that the paired plates 128*a*-128*a*, 128*b*-128*b*, 128*c*-128*c*, 128*d*-128*d* are mounted on the inside, or facing, surfaces 706 of the sensor probes 121, 122.

In the embodiment of FIG. 7B, the soil moisture sensor 100' is structured and operates similarly except that the paired plates 128'*a*-128'*a*, 128'*b*-128'*b*, 128'*c*-128'*c*, 128'*d*-128'*d* are located on the outside surfaces 709, or the surfaces that face away from one another. Some types of soil tend to expand and contract to a greater degree over time or when the weather changes. The contraction may occur between the two sensor probes 121', 122', outside the sensor probes 121', 122', or both between and outside the sensor probes 121', 122'.

When this soil contraction happens, it is possible for one side of the sensor probe to no longer contact the soil. This condition creates an air gap that causes capacitance to no longer be measurable because the air gap is, effectively, a thick insulator that defeats the capacitance effect between the conductive plates. Placing the electrically conductive plates on the "outside" 709 of the sensor probes 121', 122' as shown in FIG. 7B will permit capacitance measurement in the event of soil contraction. Note that, in the embodiment of FIG. 7B, only the placement of the electrically conductive plate(s) 128'*a*-128'*d* on the charging side is particular. The electrically conductive plates 128'*a*-128'*d* on the ground side may be placed more loosely.

It also possible to merge the two approaches shown in FIG. 7A and FIG. 7B. FIG. 7C illustrates such an approach. The soil moisture sensor 100" includes two sensor probes 121", 122". Each of the sensor probes 121", 122" includes electrically conducting plates 128*a*-128*d* mounted on the inside surface 706 thereof and electrically conducting plates 128'*a*-128'*d* mounted on the outside surface 709. This "merged" approach is particularly useful in situations where soil contraction may occur either between the sensor probes 121", 122" or outside the sensor probes 121", 122". The approach is also useful where it is anticipated that soil contraction is expected to happen both between and outside the sensor probes 121", 122". In each embodiment shown in FIG. 7A-FIG. 7C, both the charging side and the ground side include multiple electrically conductive plates. However, some embodiments may provide only a single electrically conductive plate on a single side of one or both of the sensor probes. Those in the art may realize still other variations with the benefit of this disclosure.

The placement and the charging sequence of the electrically conductive plates, however, does affect calibration. To speed up sensor operating time, multiple electrically conductive plates on the inside and the outside of the charging sensor probe as in the embodiment of FIG. 7C can be charged up simultaneously, but when this is done, additional data processing needs to be done using a calibration look-up-table approach depending on the combination and permutation of conductive plates being charged simultaneously.

Figure 8:
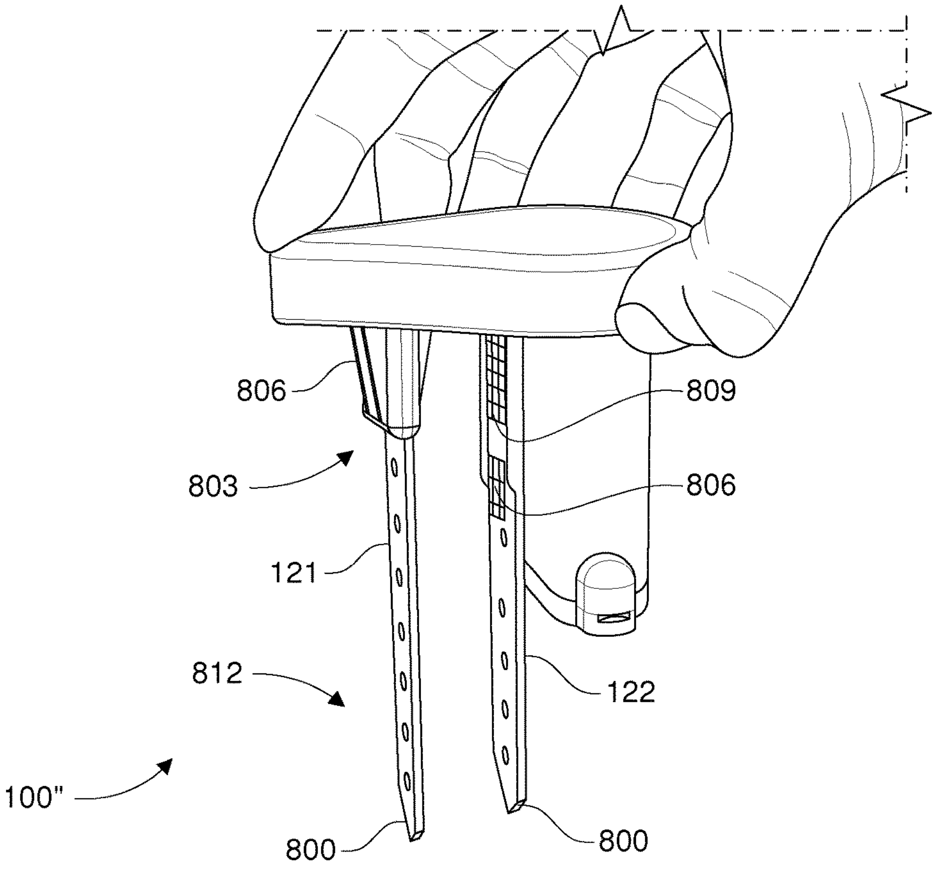
FIG. 8 depicts one way in which the soil moisture sensor may be gripped for insertion into the ground.

FIG. 8 depicts one way in which the soil moisture sensor may be gripped for insertion into the ground. FIG. 8 illustrates another embodiment of the soil moisture sensor 100" in which the sensor probes 121, 122 are structurally supported at their base ends 803 (i.e., the end most proximate the chassis cap 109) by a respective boot 806. Note the presence of the channel 809 that may permit removal of the sensor probe 122 from its respective boot 806 should it be desirable to replace or remove the sensor probe 122. The boot 806 for the sensor probe 121 is also equipped with a channel 809 not shown in this view.

In the illustrated embodiments, ground insertion is begun by forcing the sensor probes 121, 122 into the ground. Note that the sensor probes 121, 122 each terminate at the end 812 most distal to the chassis cap 109 in sharpened or pointed fashion. The points 800 each assist the insertion by facilitating penetration of the ground. It is contemplated that this aspect of the insertion is partial, and that a digging implement (e.g., a shovel) may be used to create a cavity or hole in the ground sized appropriately (e.g., in length, width, and depth) to accommodate the compartment 115. The soil moisture sensor 100 may then be inserted until the chassis cap 109 is flush with the ground as shown in FIG. 7A and FIG. 7B.

However, it is anticipated that some insertions may involve a more brute force approach. For instance, users may partially insert the sensor probes 121, 122 as described above and then attempt insert the compartment 115 without digging the cavity or hole. This may, in some instances, involve someone stepping or standing on the partially inserted soil moisture sensor 100", for example.

To this end, the soil moisture sensor 100" has been "ruggedized" to accommodate relatively high levels of force, such as by stepping or standing on the partially inserted soil moisture sensor 100". For example, the aforementioned boots 806 first shown in FIG. 8 help structurally reinforce the sensor probes 121, 122. Additional structural reinforcement such as reinforcing bars, plastic ridges, or extra thickness, none of which are shown, for the printed circuit boards of the sensor probes 121, 122. Reinforcing structural columns (not shown) may be used in other parts of the soil moisture sensor 100", too, in the chassis cap 109 and the chassis body 103. There may also be contact points 606, shown in FIG. 6, designed around the interface perimeter 503, shown in FIG. 5, of the chassis cap 109. The contact points allow contact force to be transmitted from the chassis cap 109 directly through to the chassis body 109 and then to the soil.

Ruggedization extends to materials selection in the illustrated embodiments. For example, plastic components such as the chassis cap 109, the compartment 115, and the cover plate 118, all shown in FIG. 1A-FIG. 2, may be constructed of an impact resistant, automobile grade acrylonitrile styrene acrylate ("ASA"), sometimes also called acrylic styrene acrylonitrile. ASA is an amorphous thermoplastic which has a relatively high resistance to weathering from sunlight and moisture. Fasteners and closers may be made from, for example, machine-grade 316 stainless steel and the printed circuit boards of the sensor probes 121, 122 may be fabricated from aerospace-grade G10 fiberglass.

Those in the art may appreciate still other materials choices in different embodiments. These and other materials choices are selected for their durability and resistance to environmental stresses arising from use in the outdoors, such as heat, cold, light, and moisture. Selection is also made with an eye to potentially high levels of stress that may arise from more or less forceful insertion techniques. Accordingly, the soil moisture sensor disclosed herein may, at least in some embodiments, be used in virtually any ecological environment in which insertion may be performed, such as deserts, rainforests, woodlands, prairies, etc.

The soil moisture sensor disclosed herein also includes a variety of thermal management techniques to control the heat generated by environmental and operational conditions. Referring now collectively to FIG. 1A-FIG. 3, as discussed above, the interior of the disclosed soil moisture sensor 100 is sealed from the outside environment. This means that there is no air flow for convective heat exchange. Thus, in order to increase heat exchange via conduction, the disclosed soil moisture sensor uses the power source 200, shown in FIG. 2, and sensor probes 121, 122, shown in each of FIG. 1A-FIG. 3, as heat sinks.

The main printed circuit board 312, shown in FIG. 3, has very thick power and ground planes, thicker than what is commonly found in printed circuit boards. The Copper conductors on the main printed circuit board 312 in this particular embodiment are greater than 2 oz. thick and 10 mm wide. This allows heat to conduct from all of the active components of the electronics unit 300, particularly the controller 315, into the main printed circuit board assembly on the printed circuit board 312. The power source 200 and sensor probes 121, 122 are also connected to the main printed circuit board 312 through the metal interconnects 303, 306, 309. These interconnects 303, 306, 309 help to conduct heat from the controller 315 and other active components of the electronics unit 300 into the boards of the sensor probes 121, 122 and the power source 200 which in turn conducts this heat into the ground.

Thus, the thermal subsystem features an oversized passive heatsink that efficiently redirects excess heat generated by the electronics unit 300 to the ground soil through printed circuit board 312 to one or more of the interconnects 303, 306, 309 and then to one of the sensor probes 121, 122, and thence to the ground soil.

Furthermore, to conserve and maintain the life of the power source 200, it is desirable to keep the temperature in a narrow range. By positioning the power source 200 below ground level after insertion, excess heat may be transferred to the natural thermal mass of the Earth. This keeps the power source 200 more stable than positioning the power source 200 above ground. This transfer to the Earth's thermal mass helps to limit the exposure of the power source 200 to thermal extremes. Such thermal extremes may include, by way of non-limiting example, a hot extreme from solar loading from the sun would heat and freezing from windchill effects.

In the illustrated embodiments, the soil moisture sensor uses a dual printed circuit board assembly ("PCBA") insert mold. The printed circuit boards assemblies ("PCBAs") are set into the injection molding tooling, then the plastic is injected and cools into place, thus embedding the PCBAs into the plastic of the chassis 103. This provides the PCBAs a robust attachment to the chassis 103 and prevents the PCBAs from being forced further into the chassis, or pulled out, from the forces incurred in use. In addition, the plastic-to-PCBA interface aids in creating the environmental seal for our system. The sensor PCBAs are also designed so that they can only be placed into the injection molding tooling in one direction. This helps ensure that the PCBAs are installed in reverse.

The presently disclosed soil moisture sensor permits and facilitates a collaborative environment between the soil sensor device and one or more remote computing systems. Some computational work is performed on sensor, such as, and without limitation, sensor calibration, sensor correction, and noise rejection. In some embodiments, on sensor computations may include, again without limitation, soil water moisture density, soil field capacity, soil moisture evaporation rate, soil water run-off rate, and any other soil moisture and moisture related properties and characteristics.

FIG. 9 depicts a use scenario 900 in which a soil moisture sensor 100 is inserted into the ground 700 and is communicating soil moisture data off sensor to a remote computing system 903 through a communications system 906 in accordance with one or more embodiments. The wireless communications links 909 may be implemented using any suitable wireless communication technology or protocol known to the art. As discussed above, suitable wireless communication technologies include, but are not limited to, BLUETOOTH®, cellular network, WIFI®, IEEE802.11, RF4CE, and/or IEEE802.15.4.

The communication system 906 may comprise one or more systems. For example, the communication system 906 may include a private network, such as a local area network ("LAN"), that communicates over a public network (e.g., the Internet). Or, the communication system 906 may just comprise a public network like the Internet. In this scenario the soil moisture sensor 100 may communicate directly with the remote computing system 903 directly over the public network.

The remote computing system 903 is "remote" in the sense that it is located at a site 905 that is not in the physical presence of the soil moisture sensor 100. The soil moisture data is transmitted to the remote computing system 903, which can process, archive, analyze, and/or display the data. The remote computing system 903 can also perform any or all of these functions in combination. The remote computing system 903 may be, for example and without limitation, a cloud.

As discussed above, the soil moisture system 100 includes four vertically distributed parallel plate capacitors 720*a*-720*d*, shown best in FIG. 7A, although other embodiments may employ different numbers of parallel plate capacitors. Thus, in the illustrated embodiment, the soil moisture sensor data is divided into four distinct domains, each domain being defined at a depth by the parallel plate capacitor 720*a*-720*d* from which it is being sensed. This allows the soil moisture sensor 100 to measure accurate moisture data as a function of depth. This functionality, in turn, allows calculation of both the surface moisture as well as the root level moisture. Although this embodiment aggregates this into two different values "surface" and "root" moisture, having these four domains allows the entire gradient of moisture across the entire sensor length. From this moisture gradient, one may identify drying trends so that the system can predict the need for watering and give more accurate watering suggestions for users. In addition, the surface area of the capacitance domains are surface area matched, for more system accuracy.

Referring collectively to FIG. 3, FIG. 7A, and FIG. 9, to sense the moisture, the electronics unit 300, shown in FIG. 3, cyclically charges the parallel plate capacitors 720*a*-720*d* and allows them to discharge. The rate of discharge is directly proportional to the amount moisture in the soil 703. The controller 313 then collects the discharge information to determine the amount moisture whereby the data is then transmitted off sensor over the communications system 906 to the remote computing system 903.

As discussed above, the charging side is cyclically charged and allowed to discharge. The discharge rate (RC decay rate) is then measured by analog-to-digital ("A/D") circuitry ("ADC"). The circuitry can be implemented with any kind of oscillator electronics, whether active or passive. One particular implementation uses an active oscillator ADC circuitry based on 555-Timer Astable clock circuitry. The oscillation circuitry generates a clock signal as a function of the RC charge decay rate. The clock frequency is then measured by the processor module using any kind of common pulse-counter measurement technique. The measured clock frequency then can be mathematically translated (based on a predetermined translation function unique to the RC circuitry implemented) to determine the capacitance value measured by the sensor probes. An oscillation frequency of at least 1 MHz or higher is chosen as soil moisture to dielectric relationship becomes extremely non-linear at any lower frequency. Finally, frequency lower than 1 GHz is chosen since any frequency above 1 GHz is extremely power hungry and becomes suboptimal to use in a remote sensor device that is locally powered.

In the illustrated embodiments, there are multiple sensor patches defining multiple capacitors per probe. Since the sensor patches are relatively close to each other in these embodiments, no two adjacent sensor patches are measured simultaneously in these embodiments as this helps minimize electrical noise and interference due to magnetic field coupling between two nearby capacitors.

Figure 10:
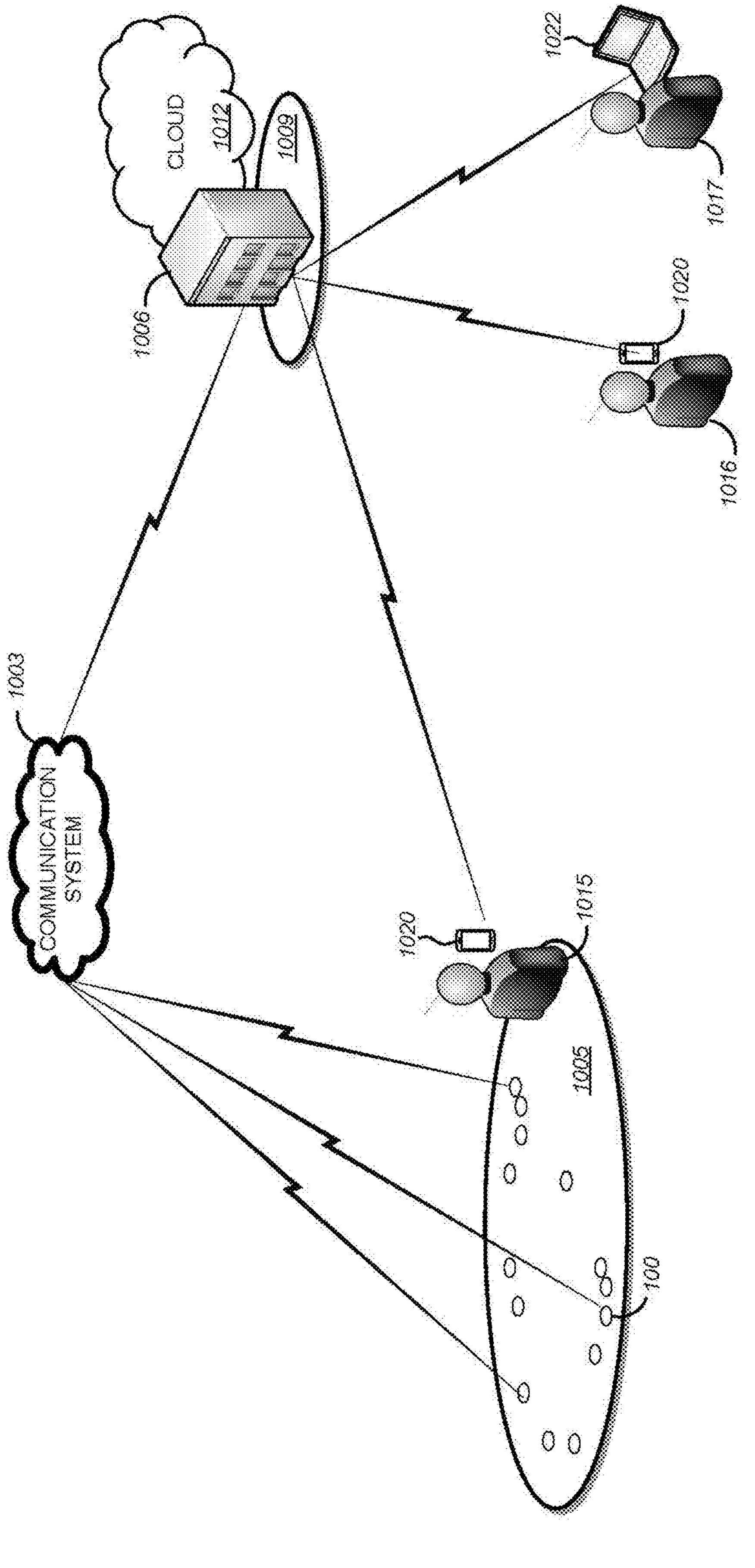
FIG. 10 depicts a plurality of inserted soil moisture sensors acquiring soil moisture data and transmitting it off sensor over a communications system to a remote computing system in accordance with one or more embodiments.

FIG. 10 depicts a scenario 1000 in which a plurality of inserted soil moisture sensors 100, only one indicated, are acquiring soil moisture data in a preselected area 1005 and wirelessly transmitting the soil moisture data off sensor. The soil moisture data is transmitted over a communications system 1003 to a remote computing system 1006 in accordance with one or more embodiments. The communication system 1003 is, in this particular embodiment, the Internet. The remote computing system 1006 is located at a site 1009 removed from, or not in the physical presence of, the preselected area 1005. In this particular embodiment, the remote computing system 1006 is a cloud 1012.

The scenario 1000 contemplates that a plurality of users 1015-1017 log into a portal (not shown) in cloud 1012 through which they may access the soil moisture data. Although the users 1015-1017 are shown using mobile computing devices—e.g., smart phones 1020 and a laptop 1022, the scenario is not so limited and other types of computing devices such as, without limitation, workstations, desktops, etc. The users 1015-1017 may then perform a variety of tasks such as alter or implement watering schedules, recognizing the need for maintenance or replacement of individual soil moisture sensors 100, and other such tasks.

Figure 11A:
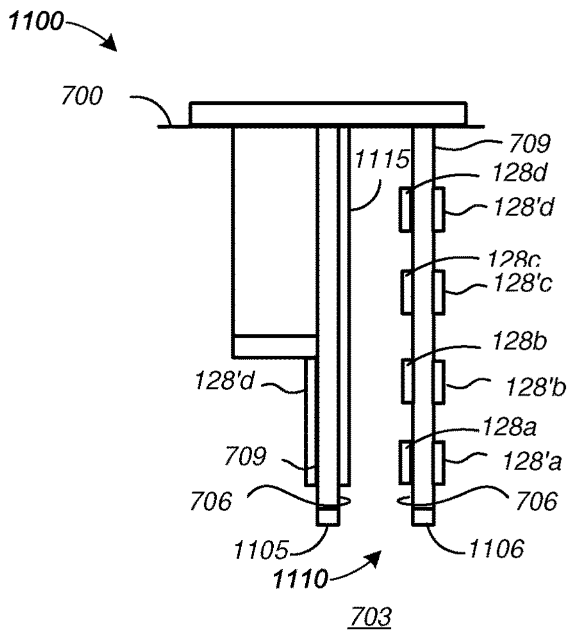
FIG. 11A and FIG. 11B depict one particular implementation of a soil moisture sensor in accordance with one or more embodiments in a perspective view showing the chassis and the parallel plate capacitance sensing element.
Figure 11B:
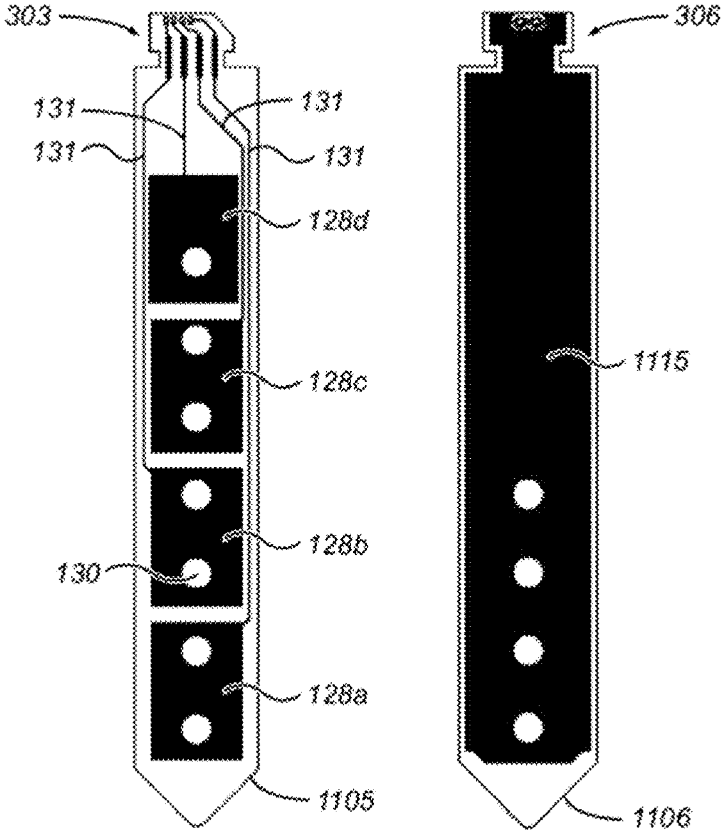

As noted above, those skilled in the art having the benefit of this disclosure may realize still other variations. For example, FIG. 11A and FIG. 11B depict one particular implementation of a soil moisture sensor 1100 in accordance with one or more embodiments in a perspective view showing the chassis and the parallel plate capacitance sensing element. The soil moisture sensor 1100 includes two sensor probes 1105, 1106. Sensor probe 1106 is the charging side and sensor probe 1105 is the ground side of the sensing element 1110.

As in the embodiment of FIG. 7C, the sensor probe 1106 on the charging side includes a plurality of electrically conductive plates 128*a*-128*d* disposed on the "inside" surface 706 and a plurality of electrically conductive plates 128'*a*-128'*d* disposed on the "outside" surface 709. Note that the positions of the electrically conductive plates 128*a*-128*d* and 128'*a*-128'*d* relative to the surfaces vary somewhat relative to the embodiment of FIG. 7C. The sensor probe 1105 on the ground side, however, includes only a single electrically conductive plate 1115 on the inside surface 706 and a single electrically conductive plate 1120 on the outer surface 709. Note how the single electrically conductive plate 1115 eliminates the need for electrical traces as the electrically conductive plate 1115 may be wired directly to the electrical interconnects 306.

Accordingly, in various embodiments, the number and positions of the electrically conductive plates may vary. Similarly, the number and positions of the electrically conductive plates on the two sensor probes need not mirror each other as shown in FIG. 7A and FIG. 7B, but may vary as shown in FIG. 7C. Although not shown in the drawings, the geometry and techniques by which the electrically conductive plates are disposed upon the printed circuit boards of the sensor probes may also vary. Those skilled in the art having the benefit of this disclosure may realize still other variations.

In the course of the detailed description above, the soil moisture system at various is identified as being adapted for, or adapted to, ground insertion. This adaptation may be implemented in one or more of several ways. For example, the tips of the sensor probes are sharpened or pointed, which facilitates insertion. Although not shown herein, the external, outer, or lower side of the cover plate may be similarly shaped to facilitate insertion and thereby adapt the soil moisture sensor for Unless a term is expressly defined herein using the phrase "herein", or a similar sentence, there is no intent to limit the meaning of that term beyond its plain or ordinary meaning. To the extent that any term is referred to in this document in a manner consistent with a single meaning, that is done for sake of clarity only; it is not intended that such claim term be limited to that single meaning. Finally, unless a claim element is defined by reciting the word "means" and a function without the recital of any structure, it is not intended that the scope of any claim element be interpreted based on the application of 35 U.S.C. § 112(f).

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

As used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

As used herein, to "provide" an item means to have possession of and/or control over the item. This may include, for example, forming (or assembling) some or all of the item from its constituent materials and/or, obtaining possession of and/or control over an already-formed item.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted. In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto.

Use of the phrases "capable of," "capable to," "operable to," or "configured to" in one or more embodiments, refers to some apparatus, logic, hardware, and/or element designed in such a way to enable the use of the apparatus, logic, hardware, and/or element in a specified manner. Use of the phrase "exceed" in one or more embodiments, indicates that a measured value could be higher than a pre-determined threshold (e.g., an upper threshold), or lower than a pre-determined threshold (e.g., a lower threshold). When a pre-determined threshold range (defined by an upper threshold and a lower threshold) is used, the use of the phrase "exceed" in one or more embodiments could also indicate a measured value is outside the pre-determined threshold range (e.g., higher than the upper threshold or lower than the lower threshold).

The subject matter of the present disclosure is provided as examples of apparatus, systems, methods, circuits, and programs for performing the features described in the present disclosure. However, further features or variations are contemplated in addition to the features described above. It is contemplated that the implementation of the components and functions of the present disclosure can be done with any newly arising technology that may replace any of the above-implemented technologies.

The detailed description is made with reference to the accompanying drawings and is provided to assist in a comprehensive understanding of various example embodiments of the present disclosure. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments. In addition, descriptions of well-known functions and constructions may be omitted for clarity and conciseness. Accordingly, those of ordinary skill in the art will recognize that various changes and modifications of the examples described herein can be made without departing from the spirit and scope of the present disclosure.

Various modifications to the disclosure will therefore be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

What is claimed is:

1. A soil moisture sensor, comprising:

a power source;

a parallel plate capacitance sensing element powered by the power source and adapted for ground insertion to generate and transmit capacitance data, the sensing element including a pair of mutually facing sensor probes, each sensor probe oriented in a respective vertical plane, the respective vertical planes being parallel with respect to one another; and an electronics unit powered by the power source to:

receive the capacitance data transmitted from the parallel plate capacitance sensing element;

process the received capacitance data; and communicate the processed capacitance data off the sensor.

2. The soil moisture sensor of claim 1, wherein each sensor probe further comprises:

a printed circuit board;

at least one electrically conductive plate mounted thereon paired with another electrically conductive plate mounted to the other sensor probe to define a parallel plate capacitor; and an electrical trace formed in or on the printed circuit board and extending from the electrically conductive plate to the electronics unit.

3. The soil moisture sensor of claim 2, wherein:

the electrically conductive plate is one of a plurality of electrically conductive plates separately mounted on the printed circuit board;

the electrical trace is one of a plurality of electrical traces, each electrical trace extending from a respective one of the electrically conductive plates to the electronics unit; and the plurality of electrically conductive plates defining a plurality of parallel plate capacitors.

4. The soil moisture sensor of claim 3, wherein the electrically conductive plates are diametrically disposed on the facing sides of the sensor probes.

5. The soil moisture sensor of claim 3, wherein the plurality of parallel plate capacitors are vertically stacked, each parallel plate capacitor acquiring the capacitance data at a respective depth when in use.

6. The soil moisture sensor of claim 3, wherein the electrically conductive plates are disposed on the sides of the sensor probes opposite the facing sides of the sensor probes.

7. The soil moisture sensor of claim 1, further comprising a chassis, the chassis including:

a chassis cap in which the electronics unit is disposed; and a chassis body in which the power source is disposed;

the chassis being sealed against fluid penetration.

8. The soil moisture sensor of claim 1, wherein the electronics unit comprises:

a communications interface;

a sensor interface; and a processor-based resource that receives the capacitance data through the sensor interface and transmits the received capacitance data off the sensor through the communications interface.

9. The soil moisture sensor of claim 8, wherein the processor-based resource is a microprocessor.

10. A method for monitoring soil moisture, comprising:

disposing a soil moisture sensor in the ground, the soil moisture sensor comprising a parallel plate capacitance sensing element including a parallel plate capacitor;

capacitive displacement sensing over free space, the sensing including cyclically charging and discharging the parallel plate capacitor of the parallel plate capacitance sensing element;

determining the soil moisture from the capacitance characteristics of the parallel plate capacitor as the parallel plate capacitor is cyclically charged and discharged; and transmitting the determined soil moisture off the sensor.

11. The method of claim 10, wherein the soil moisture sensor comprises:

a power source;

a parallel plate capacitance sensing element powered by the power source and adapted for ground insertion to generate and transmit capacitance data, the sensing element including a pair of mutually facing sensor probes, each sensor probe oriented in a respective vertical plane, the respective vertical planes being parallel with respect to one another; and an electronics unit powered by the power source to:

receive the capacitance data transmitted from the parallel plate capacitance sensing element;

process the received capacitance data; and communicate the processed capacitance data off the sensor.

12. The method of claim 10, wherein disposing the soil moisture sensor in the ground includes positioning the parallel plate capacitor at least 0.5" to 4" beneath the ground surface.

13. The method of claim 10, wherein disposing the soil moisture sensor in the ground includes disposing a power source for the soil moisture sensor housed in a chassis body thereof below the ground surface.

14. The method of claim 10, wherein:

the parallel plate capacitor is one of a plurality of parallel plate capacitors;

the plurality of parallel plate capacitors are disposed vertically on the sensor probes such that, when the soil moisture sensor is disposed in the ground, the parallel plate capacitors are disposed at different depths in the soil; and the method further comprises, cyclically charging and discharging each of the parallel plate capacitors; and determining the soil moisture at the different depths from the capacitance characteristics of the parallel plate capacitors as the parallel plate capacitors are cyclically charged and discharged.

15. The method of claim 10, wherein transmitting the determined soil moisture off the sensor includes transmitting the determined soil moisture wirelessly.

16. A system for monitoring soil moisture in a preselected area, the system comprising:

a plurality of soil moisture sensors disposed in the ground in the preselected area, each of the soil moisture sensors further comprising:

a power source;

a parallel plate capacitance sensing element powered by the power source and adapted for ground insertion to generate and transmit capacitance data from a plurality of depths at the respective location of the soil moisture sensor, the sensing element including a pair of mutually facing sensor probes, each sensor probe oriented in a respective vertical plane, the respective vertical planes being parallel with respect to one another; and an electronics unit powered by the power source to:

receive the capacitance data transmitted from the parallel plate capacitance sensing element;

process the received capacitance data; and communicate the processed capacitance data off the sensor;

a communications system over which each soil moisture sensor transmits the respective soil moisture data; and a remote computing system receiving the transmitted soil moisture data over the communications system and monitoring the soil moisture condition of the preselected area.

17. The system of claim 16, wherein each sensor probe further comprises:

a printed circuit board;

a plurality of electrically conductive plates mounted thereon, each electrically conductive plate forming a parallel plate capacitor with a respective electrically conductive plate disposed on the paired sensor probe such that the parallel plate capacitors are disposed at different depths in the soil;

a plurality of electrical traces formed in or on the printed circuit board and extending from a respective one of the electrically conductive plates to the electronics unit; and the electrically conductive plates defining a parallel plate capacitor.

18. The system of claim 16, wherein the communications system is a public network or a private network.

19. The system of claim 16, wherein the remote computing system is a plurality of cloud-based resources.

20. A method for monitoring soil moisture, comprising:

disposing a plurality of soil moisture sensors in the ground in a preselected area, each of the soil moisture sensor comprising a parallel plate capacitance sensing element including a plurality of parallel plate capacitors disposed at different depths in the soil;

capacitive displacement sensing over free space, the sensing including cyclically charging and discharging the parallel plate capacitors of the parallel plate capacitance sensing elements;

determining the soil moisture from the capacitance characteristics of the parallel plate capacitors as the parallel plate capacitors are cyclically charged and discharged; and transmitting the determined soil moisture off the sensor over a communications system to a remote computing system for monitoring.

21. The method of claim 20, wherein the communications system is a public network or a private network.

22. The method of claim 20, wherein the remote computing system is a plurality of cloud-based resources.

* * * * *